(12) United States Patent
Rothenfusser et al.

(10) Patent No.: US 7,064,331 B2
(45) Date of Patent: Jun. 20, 2006

(54) METHOD FOR CALIBRATING AND ENHANCING FLAW DETECTION OF AN ACOUSTIC THERMOGRAPHY SYSTEM

(75) Inventors: Max Rothenfusser, Munich (DE); Christian Homma, Munich (DE); Paul John Zombo, Cocoa, FL (US); Paul D. Vona, Cocoa, FL (US); Robert E. Shannon, Export, PA (US)

(73) Assignee: Siemens Power Generation, Inc., Orlando, FL (US)

( * ) Notice: Subject to any disclaimer, the term of this patent is extended or adjusted under 35 U.S.C. 154(b) by 328 days.

(21) Appl. No.: 10/667,262

(22) Filed: Sep. 19, 2003

(65) Prior Publication Data

US 2004/0056200 A1    Mar. 25, 2004

Related U.S. Application Data

(63) Continuation-in-part of application No. 10/243,009, filed on Sep. 13, 2002.

(51) Int. Cl.
*G01N 21/70* (2006.01)

(52) U.S. Cl. .................................. 250/341.6; 250/341.1
(58) Field of Classification Search ............. 250/341.1, 250/341.6
See application file for complete search history.

(56) References Cited

U.S. PATENT DOCUMENTS

| | | | |
|---|---|---|---|
| 3,511,086 A | 5/1970 | Woodmansee | |
| 4,578,584 A | 3/1986 | Baumann et al. | |
| 4,607,341 A | 8/1986 | Monchalin | |
| 4,866,276 A * | 9/1989 | Leavens et al. | 250/341.6 |
| 5,111,048 A | 5/1992 | Devitt et al. | |
| 5,834,661 A * | 11/1998 | Nonaka et al. | 73/866 |
| 6,236,049 B1 * | 5/2001 | Thomas et al. | 250/341.6 |
| 6,367,969 B1 | 4/2002 | Ringermacher et al. | |
| 6,394,646 B1 * | 5/2002 | Ringermacher et al. | 374/7 |
| 6,495,833 B1 | 12/2002 | Alfano et al. | |
| 2002/0121602 A1 | 9/2002 | Thomas et al. | |
| 2004/0051035 A1 * | 3/2004 | Zombo et al. | 250/252.1 |
| 2004/0089811 A1 * | 5/2004 | Lewis et al. | 250/341.6 |
| 2004/0149021 A1 * | 8/2004 | Kessler et al. | 73/105 |

FOREIGN PATENT DOCUMENTS

SU    1200675 A1    7/1990

* cited by examiner

*Primary Examiner*—Albert Gagliardi

(57) ABSTRACT

A method and apparatus for calibrating an acoustic thermography system 10 and/or enhancing the flaw detection abilities of such a system is provided. The method allows applying a material (e.g., 103) to a specimen 12 undergoing acoustic thermography inspection. The material is thermally responsive to acoustic energy transmitted to the specimen by the acoustic thermography system. In one aspect thereof, a thermal response of the material applied to the specimen when subjected to acoustic energy is processed to determine whether the level of acoustic energy applied by the acoustic thermographic system appropriately meets a desired amount of acoustic energy for inspecting the specimen. In another aspect thereof, the thermal response of the specimen in combination with the applied material may be processed to determine whether certain types of flaws (e.g., relatively wide flaws) are actually present in the specimen or to enhance the detectability of other flaws that would only faintly show up on the infrared images.

15 Claims, 2 Drawing Sheets

METHOD FOR CALIBRATING AND ENHANCING FLAW DETECTION OF AN ACOUSTIC THERMOGRAPHY SYSTEM

This application is a Continuation-In-Part of U.S. application Ser. No. 10/243,009 filed Sep. 13, 2002.

FIELD OF THE INVENTION

This invention relates generally to the field of acoustic thermography and more particularly to techniques for calibrating and enhancing flaw detection of an acoustic thermography system.

BACKGROUND OF THE INVENTION

There are many known techniques for nondestructively examining a test specimen, such as a turbine blade. Many of these techniques involve introducing energy into the specimen and detecting a modified form of that energy as it leaves the specimen. For example, it is known to apply X-ray, ultrasonic, magnetic, or heat energy into a test specimen and to detect flaws in the specimen as perturbations in the respective energy pattern as it returns from the specimen.

Acoustic thermography is one such form of nondestructive examination that involves the application of acoustic energy to a test specimen and the measurement of heat energy that is generated within the specimen as a result of the acoustic energy interacting with a flaw, e.g., a crack. Under one of several plausible physical mechanisms for heating, it is believed that as acoustic energy passes through the material of a specimen, opposing surfaces of a crack or other flaw may rub together, thus generating heat. Because undamaged areas of the specimen are only minimally heated by the acoustic waves, a thermal image of the specimen will reveal the flawed area as exhibiting an increase in temperature.

The effectiveness of an acoustic thermography examination is related to the efficiency of the input of acoustic energy into the test specimen. Thus, a means for quickly and reliably determining a sufficient amount of energy transfer into the specimen is desired. Although accelerometers and laser-based vibrometers are accurate devices for determining the amount of acoustic energy applied to the specimen, undesirably, such devices tend to be expensive, cumbersome, and time-consuming for deployment in industrial applications.

In known acoustic thermography techniques, it has been observed that just relatively tight flaws appropriately heat up to become detectable. That is, relatively wide, open voids or cracks may not sufficiently heat up under known acoustic thermography techniques. It would be desirable to provide relatively inexpensive techniques that would systematically allow for these wide voids or flaws to become visible during acoustic thermography.

SUMMARY OF THE INVENTION

Generally, the present invention fulfills the foregoing needs by providing in one aspect thereof, a method for calibrating an acoustic thermography system. The method allows applying a material to a specimen undergoing acoustic thermography inspection. The material is thermally responsive to acoustic energy transmitted to the specimen by the acoustic thermography system. A thermal response of the material applied to the specimen when subjected to acoustic energy is processed to determine whether the level of acoustic energy applied by the acoustic thermographic system appropriately meets a desired amount and/or vibration mode characteristics of acoustic energy for inspecting the specimen.

In another aspect thereof, the present invention further fulfills the foregoing needs by providing a method for enhancing the ability of an acoustic thermography system to detect flaws in a specimen undergoing inspection. The method allows applying a material to a specimen undergoing acoustic thermography inspection. The material is thermally responsive to acoustic energy transmitted to the specimen by the acoustic thermography system particularly in the presence of at least certain types of flaws that may be present in the specimen. A thermal response of the specimen in combination with the applied material is processed to determine whether certain types of flaws are actually present in the specimen. This enhancement may be of interest for detecting defect types that may not be typically responsive to acoustic thermography inspection.

BRIEF DESCRIPTION OF THE DRAWINGS

These and other advantages of the invention will be more apparent from the following description in view of the drawings that show.

DETAILED DESCRIPTION OF THE INVENTION

Figure 1:
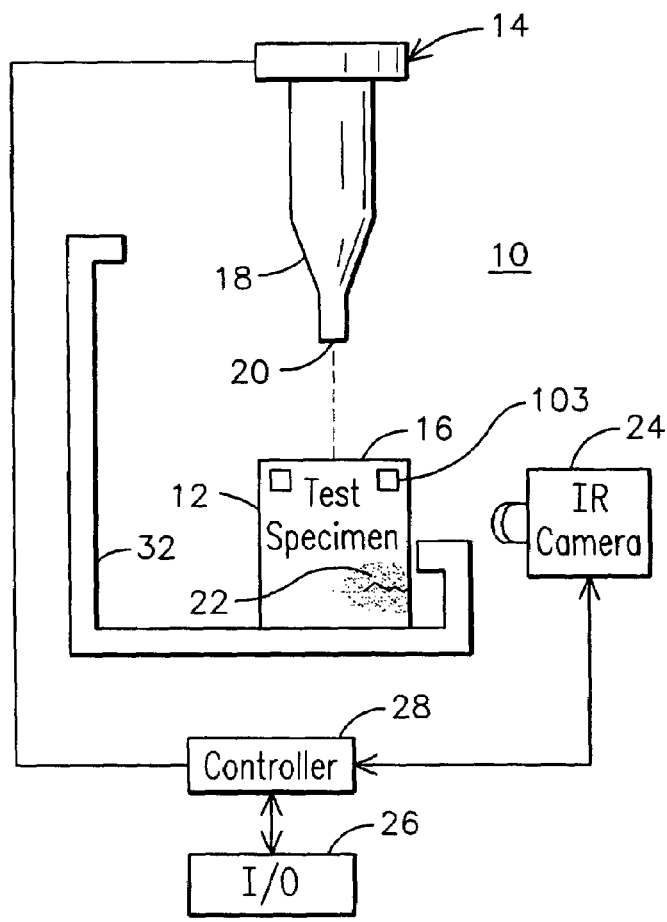
FIG. 1 is a schematic diagram of an exemplary system for performing acoustic thermography.

An exemplary system 10 used for nondestructive testing of a test specimen 12 is illustrated in schematic form in FIG. 1. The system includes an acoustic energy source 14 for delivering acoustic energy to a surface 16 of the specimen 12, as the specimen is held in a fixture 32. The type of specimens that may be inspected may be the type where a failure could cause operational issues, for example, heat exchanger tubes and other metal components used in nuclear and other types of steam generators, power generation gas turbines and steam turbines, electrical generators, aircraft parts, aerospace, automotive, manufacturing, electronics, marine, construction parts and the like.

The acoustic energy source 14 may be an ultrasonic piezoelectric device. The acoustic energy may be transferred through a probe tip such as horn 18 having a face 20 for making contact with specimen surface 16. Vibrations within the specimen 12 will cause localized heating in an area 22 surrounding a crack in the specimen 12. The increased temperature of area 22 is detected by a thermal imaging apparatus 24 (e.g., an infrared camera) for generating an image responsive to a temperature profile of the specimen 12 under influence of the acoustic energy.

Prior to the present invention, voids, pits, porosity and other open gross discontinuities generally have not been well suited to this examination method unless they have a defect with contacting surfaces associated with them. The discontinuities that have traditionally favored thermosonic imaging have been cracks, laminations, bond-line issues, and other types of discontinuities that either allow for the friction of faying surfaces or the stress concentration at notch areas.

The imaging apparatus in one exemplary embodiment may sense infrared emissions in the 3–5 micrometer wavelength and may generate images at about 100 frames per second displayed at a monitor 26, such as may be part of a personal computer. What will be seen in the monitor 26 will be a gray-scale or color representation of a thermal image as detected by the thermal imaging apparatus. A controller 28 is used to control the operation of the various components of the system 10.

The controller could be any computer, microprocessor or automated control system suitable for any given application. In one exemplary embodiment, when the detection process is initiated, the controller causes the camera to begin taking sequential images of the specimen at a predetermined rate. Once the sequence of images is initiated, the controller may transmit a signal to an amplifier that causes the amplifier to send a pulse to the transducer to generate a pulsed ultrasonic signal. The ultrasonic energy may be in the form of a pulse at a given frequency. After the end of the pulse, the controller may command the camera to stop taking images. The images generated by the camera may be transmitted to the monitor to be displayed. The images may also be sent to a storage device to be viewed at another location or at a later time if so desired.

The description provided so far constitutes general background information descriptive of an exemplary operational environment of the present invention as further elaborated below. For readers desirous of additional background information, reference is made to U.S. patent application Ser. No. 10/243,009 filed Sep. 13, 2002 titled "Reference Standard Systems For Thermosonic Flaw Detection," which application is commonly assigned to the same assignee of the present invention and is herein incorporated by reference.

The inventors of the present invention have innovatively recognized that during acoustic thermography examinations the presence of certain materials (e.g., layers) attached to a vibrating specimen would predictably heat up due to the absorption of acoustic energy by such materials. By way of example, these materials may include adhesive materials. Commercially available adhesive tapes, which have proven to be useful include the following: Poster strips with Command™ adhesive tape available from Minnesota Mining and Manufacturing Company and Tesa brand Power Strips™ adhesive tape available from Beiersdorf AG of Hamburg, Germany.

The present invention is not limited to adhesive tape. Examples of other materials may include fluids either in gaseous or liquid form, viscoelastic materials, such as grease, wax, adhesive, honey, epoxies, paints, etc., plastic foams, powders, gases convertible into liquids, liquid-impregnated solids, and semi-solids such as putties. Preferably, the viscosity of the material should be matched to the excitation frequency in a way that an appropriate amount of acoustic energy can be absorbed and converted into heat. During the application of the acoustic energy, these materials predictably heat up, and the thermal response of such materials can be detected with the infrared camera of the acoustic thermography system to gain information that either may be used for checking quality control in an acoustic thermography examination, enhancing the detection capability of acoustic thermography, or both. Transparent adhesive tapes may be advantageous because they generate heat from work performed during plastic deformation when exposed to acoustic or ultrasonic vibrations, and they allow for viewing or partial viewing of the surface of the test part in the area of interest through the test part. Further, an adhesive tape substrate comprising intentionally-created debond flaws could be used as the flaw-enhancing material.

Placement of these materials at various locations on the specimen under examination can be used as a means of determining that a sufficient amount of acoustic energy is being introduced into the specimen. In one exemplary embodiment, one or more pieces of tape were applied to a turbine blade to be tested in a manner that ensured that they would register on the thermal image resulting upon application of acoustic energy to the blade, thereby confirming that a sufficient amount of acoustic energy had been imparted to the blade. If insufficient energy was imparted to the blade, the tape would not register on the thermal image—therefore in this embodiment the tape was being used as a quality control check. That is, placement of such materials onto the specimen and measurement of their thermal response during the application of acoustic energy would allow determining that the acoustic thermography system is appropriately functioning. Cases where such materials heat in direct proportion to the amount of vibration energy needed to cause defect heating would allow determining that the acoustic thermography system is appropriately calibrated without having to use expensive and cumbersome devices, such as laser vibrometers. Upon determining that the acoustic thermography system is appropriately calibrated, the materials attached to the test specimen would be removed and the examination of the test specimen would proceed without any delays for dismantling a calibration setup that may otherwise be necessary.

In another exemplary embodiment, the inventors of the present invention further recognized that coating the test specimen in part or entirely or allowing solid or fluid forms of the material to cover an area of interest of the test specimen allows for enhancing the infrared response at flaw locations or causing infrared responses at defect locations where no response was caused due to the nature, shape or open characteristics of the defect. One of the issues traditionally encountered in acoustic thermography is that if the defect is a wide open flaw, one may not induce sufficient friction on the opposing surfaces therebetween when the sonic energy is applied to the specimen. Thus, such wide flaws may not sufficiently heat up to become detectable by the infrared camera. The inventors of the present invention noticed that if, for example, one applied tape or other suitable flaw-enhancing material over the wide cracks, even though the surfaces therebetween may not be rubbing against one another, one would detect such flaws because the tape would heat up and the amount of heating up would be incrementally higher over the crack because there is believed to be a high degree of free motion for the tape placed at that crack in response to the vibratory excitation. More particularly, it is believed that tape over the crack may heat up because the two sides of the crack can move independently of each other and cause the tape to be stretched and compressed to an increasing degree.

In another aspect of the present invention, in lieu of using tape, one may use a fluid form of the flaw-enhancing material, e.g., a liquid, and one may immerse the specimen in the liquid (analogous to penetrant testing) and wipe off any excess material and the flaw-enhancing material would be able to penetrate into the crack. The specimen would be acoustically energized and in practice the flaw that may now be detected with the flaw-enhancing material could be a relatively wide crack. This is consistent with the underlying physics since a wide flaw is the type of flaw where the liquid would be most likely to penetrate into. The material would heat up in the crack and this provides a novel technique for finding certain type of flaws that one could not find before using traditional acoustic thermography techniques. Additionally, this technique would provide an improvement in penetrant inspection methods by using vibration energy and infrared imaging to eliminate the need for additional steps involving application of penetrant developers. By way of example, the fluid may be drawn into the flaw due to capillary and/or surface tension forces.

A wide flaw may be a flaw where the opposing surfaces of the flaw may not touch one another in their ambient state, and/or where the opposing surfaces are separated by a distance exceeding the local vibration amplitudes at the test frequencies being used. One example would be a separation of approximately 5 µm at 20 kHz. As a rule of thumb, the displacement of the blade during energization lies in the range of some microns (generally not more than about 5). Therefore the crack should be not larger than this range to be easily detectable. Since many cracks exhibit more or less jagged shapes the chance is good that there is at least some segment where the cracks sides are close enough to each other to produce friction. However, there may be wide open cracks that do not show such a jagged shape. These may be the type of cracks where aspects of the present invention are believed to be particularly advantageous. However, one may use the "flaw-enhancing material" technique for any type of crack. For example, even cracks that do light up under normal conditions would give a higher IR output when covered with the tape.

In operation, when a void is filled with the flaw-enhancing material, this void and/or the material therein would heat up and become visible during acoustic thermography inspection. This aspect of the invention advantageously expands the type of flaws that may now be detectable using acoustic thermography. For example, without the coating or the introduction of the flaw-enhancing material, only relatively tight cracks or voids would heat up and relatively wide, open voids would not sufficiently heat up during the acoustic thermography examination. This aspect of the present invention allows for these large flaws to become visible during the acoustic thermography examination. It is believed that the flaw-enhancing material might allow finding pits and voids in the specimen. That is, it would allow finding the type of flaws that would have been considered undetectable using standard acoustic thermography techniques.

As will be appreciated by those skilled in the art, there are many different types of flaws (e.g., pits, voids) other than cracks, and other than service-induced flaws that may develop in a given specimen. Prior to the present invention, acoustic thermography has been a technique generally suited for finding service-induced cracks since service-induced cracks tend to gradually deteriorate in-service and they are usually very tight when they first appear; whereas, manufacturing-induced cracks (e.g., hot tears, casting defects when the part is newly made) are likely to shrink open, and generally tend to form more open voids or voluminous defects, which prior to the present invention would have been virtually undetectable using traditional acoustic thermography techniques.

As suggested above, in one scenario one could immerse the entire test specimen into a liquid material. Then one would perform the acoustic thermography examination for determining whether or not the test specimen has unacceptable flaws. In another scenario, one may have clues (or simply suspect) that a given area of the test specimen may include flaws and in this scenario one would apply the flaw-enhancing material just to the suspect area. For example, one could apply the flaw-enhancing material in the form of one or more pieces of tape over the suspect area, or could apply a coating of a liquid or a semi-solid form of the flaw-enhancing material over the suspect area for verifying the presence of unacceptable flaws in the suspect area of the test specimen.

Figure 2:
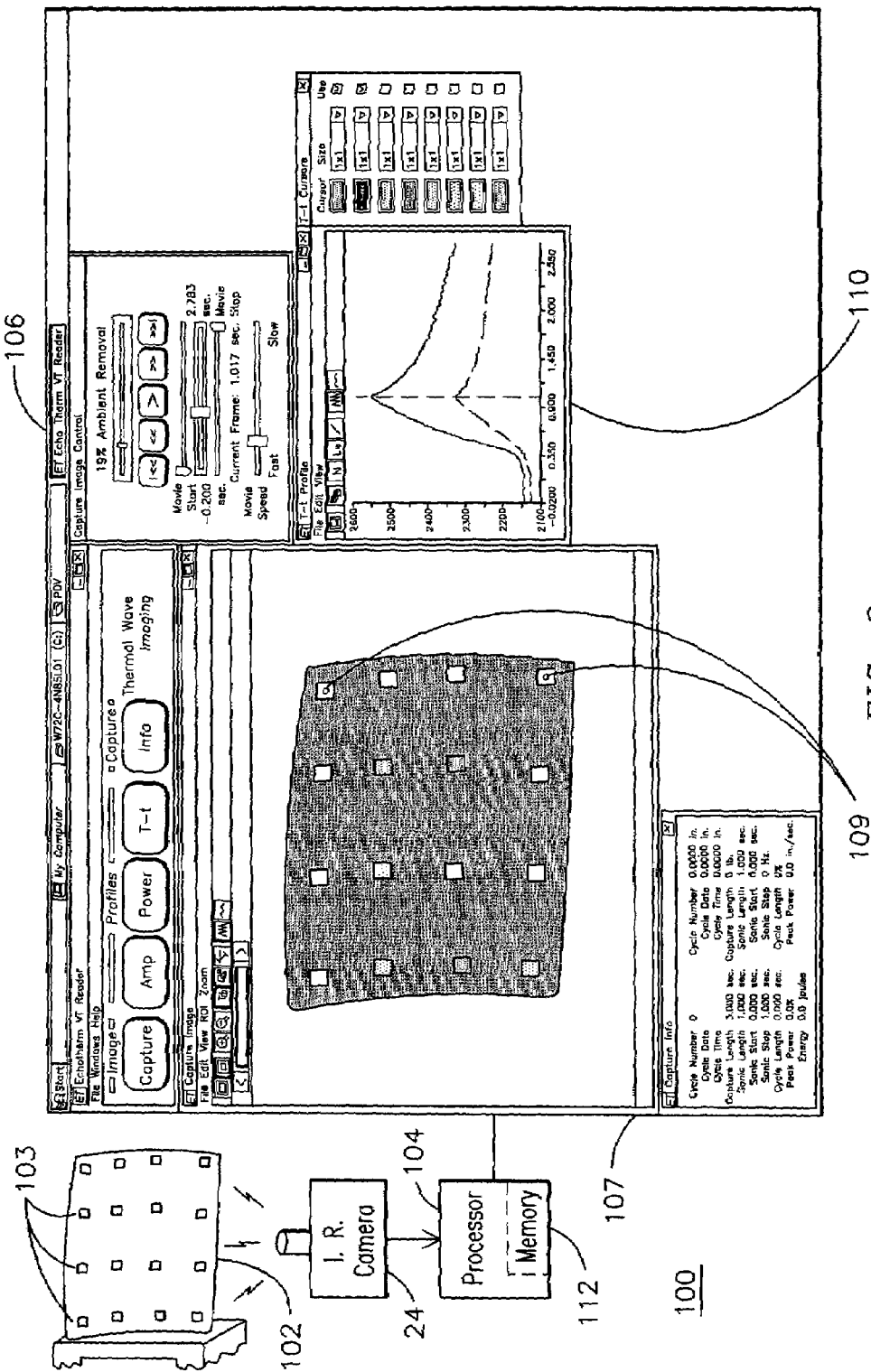
FIG. 2 is a schematic representation of a computerized system including a processor configured to process a thermal response of material applied to a test specimen undergoing inspection in accordance with aspects of the present invention.

FIG. 2 is a schematic representation of a computerized system 100 embodying aspects of the present invention. As shown in FIG. 2, a test specimen 102, such as a turbine blade, includes a material indicative of the level of acoustic energy applied to the specimen, e.g., pieces of tape 103 arranged throughout the test specimen. During application of acoustic energy to the test specimen, the infrared camera 24 is programmed to collect data indicative of the thermal response of the pieces of tape. A processor 104 is coupled to receive the thermal response data from the infrared camera and is programmed to processes the data to correlate the thermal response of the tape to the level of acoustic energy received by the test specimen.

A display 106 may be used for displaying a thermal image 107 of tape attached to the test specimen. In one exemplary embodiment, a suitable input/output device (not shown), such as a mouse, a keyboard, or pointer may be used for placing a cursor 109 onto any of the respective images of the tape and obtain a quantitative measurement of the thermal response of the tape corresponding to the image under a respective cursor.

A display window 110 may be used for displaying signal plots of the thermal response as a function of time of each image upon which a cursor has been placed. A memory 112 may be optionally provided to store a threshold value (or range of values) that may allow determining whether the measured thermal response of the tape is indicative of a sufficient amount of acoustic energy having been transferred into the test specimen.

For example, such a determination may be based on whether or not the infrared strength, (i.e. the difference between the peak value and the value at time 0) of the thermal response exceeds the threshold value stored in memory. In this case, an indication could be automatically provided to an operator indicating that the amount of acoustic energy transferred to the test specimen is sufficiently high for conducting the examination of the test specimen. Conversely, in the event the amount of acoustic energy transferred to the specimen is below the threshold level, the operator would conduct appropriate corrective actions for ensuring that the acoustic thermography system is appropriately calibrated to deliver the desired amount of acoustic energy to the specimen under test. In another embodiment, the operator may make the determination by monitoring the infrared strength of the measured thermal response and manually assessing whether such infrared strength is consistent with predefined threshold values, as may be provided in an operator's manual.

Although FIG. 2 shows a number of pieces of tape attached throughout the test specimen, it will be appreciated that the present invention is not limited to any specific number of pieces of tape, and it is contemplated that one or more pieces of tape attached to the upper edges or tip of the test specimen would be sufficient for checking that sufficient acoustic energy is applied to the specimen. During some experiments, it was observed that if a piece of tape is loosely attached to the test specimen, fluttering effects may introduce errors into the thermal response of the loosely attached tape (e.g., the thermal response would indicate higher thermal energy for a loosely attached tape). Thus, although conceptually the entire specimen could be wrapped by a large piece of flexible tape, such as textile tape, the possibility of loosely attached points throughout a fully wrapped specimen could introduce errors that may be avoided by attaching one or more small pieces of tape at a few strategic locations of the specimen, such as the upper edges or tip of the specimen.

Figure 3:
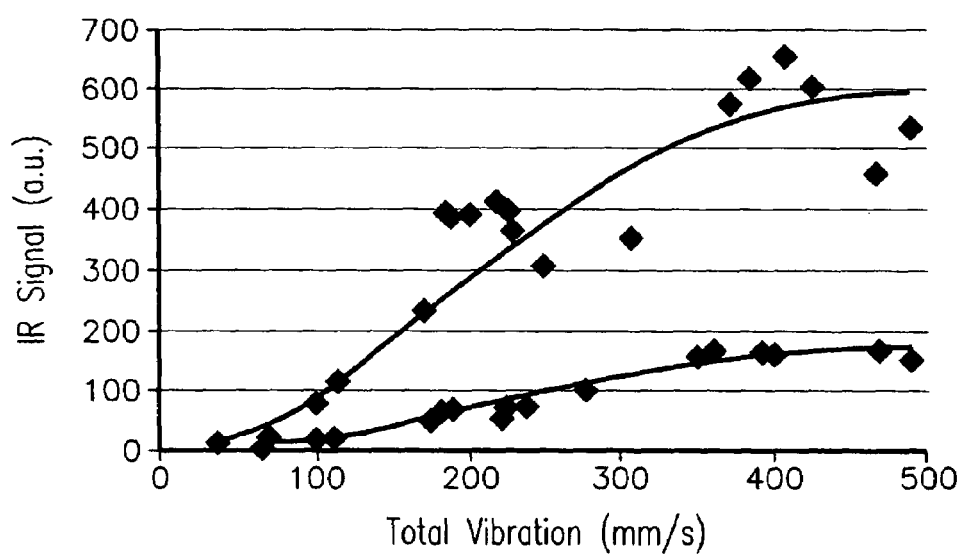
FIG. 3 show respective plots of each infrared (IR) signal amplitude obtained from two exemplary types of adhesive strips as a function of the vibratory amplitude applied to a turbine blade.

FIG. 3 shows respective plots of the IR signal amplitude obtained from two commercially available adhesive strips as a function of the vibratory amplitude applied to a turbine blade, as measured with a laser vibrometer. Experiments have shown a substantial correlation between the temperature rise at the material attached to the specimen and the amount of acoustic energy applied to the specimen, the so-called quality control check or calibration aspects of the present invention. Experiments have also shown a quantitative correlation between the temperature rise of the material over or within a wide flaw, and the ability to detect such a wide flaw in the specimen, the so-called flaw-enhancing aspects of the present invention.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

I claim as my invention:

1. A method of acoustic thermography for enhancing detection of a flaw in a specimen, said flaw of a type characterized by a void defined by mutually opposite, spaced apart surface edges, said method comprising:

applying a material to a specimen to be tested, the material being thermally responsive to acoustic energy transmitted to the specimen by an acoustic thermography system due to vibratory movement imparted to said material when engaged by the spaced apart surface edges that define the void in the specimen; and processing a thermal response of the material when acoustic energy is applied to the specimen by the acoustic thermographic system, wherein the movement imparted to said material by said spaced apart surface edges enables to generate a sufficiently intense thermal response notwithstanding that the flaw is of a type characterized by a void with spaced apart surface edges.

2. The method of claim 1 wherein the processing step comprises:

collecting data indicative of a thermal response of the material when the acoustic energy is applied; and correlating the thermal response of the material to an amount of acoustic energy applied to the specimen.

3. The method of claim 2 further comprising comparing the amount of acoustic energy applied to the specimen to a desired amount necessary for inspecting the specimen.

4. The method of claim 3 further comprising generating an indication of whether or not the amount of acoustic energy applied to the specimen appropriately meets the desired amount of acoustic energy for inspecting the specimen.

5. The method of claim 1 wherein the material comprises an adhesive tape.

6. The method of claim 1 wherein the material is selected from the group consisting of fluids, plastic foams, viscoelastic materials, powders, gases convertible into liquids, liquid-impregnated solids, and semi-solids.

7. The method of claim 1 wherein the processing step comprises:

collecting data indicative of a thermal response of the material when the acoustic energy is applied; and correlating the thermal response of the material to determine whether the flaw is present in the specimen.

8. The method of claim 7 wherein the applying step comprises:

applying a liquid form of the material; and wiping off excess liquid material from the specimen.

9. The method of claim 8 wherein the liquid is drawn into the flaw by capillary and/or surface tension forces.

10. The method of claim 7 wherein the applying step comprises applying a coating of the material to a portion of the specimen suspected of including the flaws.

11. The method of claim 7 wherein the applying step comprises applying an adhesive tape to a portion of the specimen suspected of including the flaw.

12. An acoustic thermography apparatus for enhancing detection of a flaw in a specimen, said flaw of a type characterized by a void defined by mutually opposite, spaced apart surface edges, said apparatus comprising:

an acoustic energy source for imparting acoustic energy into a specimen to be inspected;

a material adapted for application to the specimen for producing a thermal response to acoustic energy imparted to the specimen due to vibratory movement imparted to said material when engaged by the spaced apart surface edges that define the void in the specimen; and a sensor for detecting the thermal response of the material, wherein the movement imparted to said material by said spaced apart surface edges enables to generate a sufficiently intense thermal response notwithstanding that the flaw is of a type characterized by a void with spaced apart surface edges.

13. The apparatus of claim 12 wherein the material comprises an adhesive tape.

14. The apparatus of claim 12 wherein the material comprises one of the group consisting of fluids, plastic foams, viscoelastic materials, powders, gases convertible into liquids, liquid-impregnated solids and semi-solids.

15. The apparatus of claim 12 further comprising a plurality of pieces of the material for application to a selected plurality of locations on the specimen.

* * * * *